United States Patent [19]

Chupp

[11] Patent Number: 4,731,451
[45] Date of Patent: Mar. 15, 1988

[54] N-((2-OXO-3(2H)BENZOTHIAZOLYL)ME-THYL)-2-CHLOROACETANILIDES

[75] Inventor: John P. Chupp, Kirkwood, Mo.

[73] Assignee: Monsanto Company, St. Louis, Mo.

[21] Appl. No.: 133,763

[22] Filed: Mar. 25, 1980

[51] Int. Cl.$^4$ .................. C07D 263/58; C07D 277/68
[52] U.S. Cl. ...................... 548/165; 548/171; 548/221; 548/305; 71/88; 71/90; 71/92
[58] Field of Search ............ 548/165, 171, 221; 71/90

[56] References Cited

U.S. PATENT DOCUMENTS

| | | | |
|---|---|---|---|
| 3,361,752 | 1/1968 | D'Amico | 71/90 |
| 3,907,544 | 9/1975 | Olin | 71/95 |
| 3,952,056 | 4/1976 | Vogel et al. | 71/118 |
| 4,097,262 | 6/1978 | Cheng | 71/90 |
| 4,227,915 | 10/1980 | D'Amico | 548/171 |

FOREIGN PATENT DOCUMENTS

EP7772  7/1978  European Pat. Off. ............ 71/90

Primary Examiner—Glennon H. Hollrah
Assistant Examiner—D. B. Springer
Attorney, Agent, or Firm—William I. Andress

[57] ABSTRACT

The disclosure herein pertains to 2-haloacetamides characterized by substitution on the nitrogen atom of certain heterocyclymethyl radicals and by substituted or unsubstituted cycloalkenyl or phenyl radicals and to a process for the preparation thereof. These compounds are useful as herbicides.

6 Claims, No Drawings

N-((2-OXO-3(2H)BENZOTHIAZOLYL)METHYL)-2-CHLOROACETANILIDES

BACKGROUND OF THE INVENTION

1. Field of the Invention

The invention herein pertains to the field of herbicides. More particularly, the field of this invention pertains to the use of 2-haloacetamides as herbicides.

2. Description of the Prior Art

It is known in the prior art to use various 2-haloacetamides as herbicides, either individually or in combination with other herbicides.

Among herbicidal compounds of the prior art are those acetamides having in varying arrangements substitutions of alkyl, cycloalkyl, alkenyl, cycloalkenyl, alkoxy, halogen, aryl, etc. groups, all of which may be further substituted with other radicals.

Illustrative of the 2-haloacetamides of the prior art and of those most closely related to the 2-haloacetamides disclosed and claimed herein are the 2-haloacetamides disclosed in U.S. Pat. Nos. 3,495,967, 3,574,746, 3,586,496, 3,901,917, 3,819,661, 3,946,045, 4,012,222, 4,097,262, 4,055,410 and 4,155,744. In the '967 patent the 2-chloroacetamides are characterized by substitutions on the nitrogen atom including a benzothiophene radical which may have other substituents. The '746 and '496 patents are directed generally to the same 2-haloacetamides which are characterized by a $C_{5-7}$ cycloalken-1-yl group and other substituents on the amide nitrogen. The '917 patent relates to 2-haloacetanilides characterized in having a thienylmethylene group which may be substituted with a lower alkyl group substituted on the nitrogen atom and the '661 patent relates to 2-haloacetanilides which are substituted on the nitrogen atom with a furfuryl or tetrahydrofurfuryl. The '045 and '222 patents disclose 2-haloacetanilides characterized by a dioxolanyl-lower alkyl group on the anilide nitrogen atom. The '410 patent relates to 2-haloacetanilides substituted on the nitrogen atom with 2,4-dioxothiazolidinylmethyl or 2,4-dioxoimidazolidinylmethyl radicals and the '744 patent relates to 2-haloacetamides characterized by substitutions on the nitrogen atom of cycloalkenyl and heterocyclic radicals. The '262 patent relates to N-(O-substituted-phenyl)-N-[(2-oxooxazolidin-3-yl)-methyl]-2-haloacetamides.

Prior art processes for producing various 2-haloacetamides involve the haloacetylation of the appropriate aniline or cyclohexylideneimine to get the corresponding product.

As will be apparent, the most relevant 2-haloacetamides of the prior art have a heterocyclic and cycloalkenyl or phenyl (which may be substituted) group attached to acetamide or acetanilide nitrogen atom. However, this above prior art fails to disclose the novel 2-haloacetamides and process of the present invention as will be apparent from the discussion below.

SUMMARY OF THE INVENTION

The present invention relates to herbicidally active compounds, a novel process for preparing same, herbicidal compositions containing these compounds and herbidical method of use of said compositions in agricultural crops, particularly rice.

The herbicidal compounds of this invention are characterized by the formula

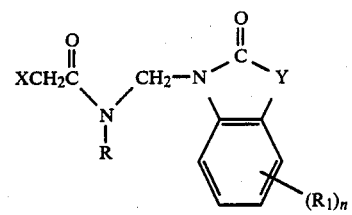

wherein
X is chlorine, bromine or iodine;
R is a $C_{5-7}$ cycloalkenyl or phenyl radical or such R radical substituted with $C_{1-6}$ alkyl, thioalkyl, alkoxy, alkoxyalkyl, polyalkoxy, $C_{2-6}$ alkenyl or alkynyl, $C_{5-10}$ aryl, halogen, $NO_2$, $CF_3$ or a $C_{5-6}$ heterocyclic ring containing O or S hetero atoms;
Y is O, S or $NR_4$; $R_4$ is hydrogen or $C_{1-4}$ alkyl;
$R_1$ is hydrogen or said radicals as may be substituted on R; and
n is an integer from 0–4 inclusive.

Compounds of particular interest include those where in the above Formula I, R is a lower alkyl- and-/or alkoxy-substituted phenyl or lower alkyl-substituted cycloalken-1-yl group and Y is sulfur.

A preferred species of this invention is N-(2,6-dimethyl-1-cyclohexen-1-yl)-N-[(2-oxo-3-(2H)-benzothiazolyl)methyl]-2-chloroacetanilide. Other species will be described below.

The novel process of this invention involves preparing the compounds of Formula I by reacting a compound of the formula

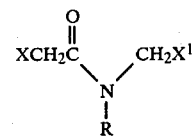

with a compound of the formula

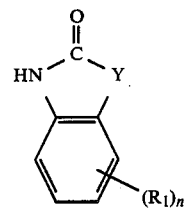

wherein $X^1$ is a halogen, X, Y, R, $R_1$ and n are as defined above, in the presence of a base and preferably in the presence of a phase transfer catalyst. The reaction is carried out at temperatures within the range 0°–120° C., preferably between 10°–60° C.

The preferred bases for use in this process are alkali metal hydroxides, although other bases such as elemental metals, metal fluorides, hydrides, oxides, carbonates or alkoxides may also be used.

Preferred phase transfer catalysts are the quaternary ammonium halide salts, e.g., aryl or aralkyl trialkyl ammonium halide salts such as benzyl triethyl ammonium bromide or chloride. Other phase transfer catalysts include the acyclic and cyclic polyethers, e.g., "18-crown-6" cyclic ethers in combination with alkali metal hydroxide as base.

The compounds of this invention are useful as herbicides.

DETAILED DESCRIPTION OF THE INVENTION

The compounds according to this invention may be prepared by alternative processes. Example 1 describes the preparation of an invention compound by using an N-alkylation process previously developed by the inventor herein. This process involves converting a sec-2-haloacetamide to an anion thereof under basic conditions, then reacting the anion with an alkylating agent, preferably in the presence of a phase transfer catalyst. The said N-alkylation process and variations thereof contributed by another employee in the laboratories of the assignee herein is the subject of copending U.S. Ser. No. 63,005 filed Aug. 2, 1979 as a continuation-in-part of U.S. Ser. No. 896,879 filed Apr. 17, 1978, now abandoned.

EXAMPLE 1

2-chloro-N-(2,6-dimethyl-1-cyclohexen-1-yl)-acetamide (4 g, 0.02 mol), 3-chloromethyl-2-benzothiazolinone (5.5 g, 0.0275 mol), benzyltriethyl ammonium bromide (2 g) and 75 ml of methylene chloride were charged to a 500 mL round bottom flask. With stirring, sodium hydroxide (15 g of 50% aqueous) was added all at once. Stirred one hour. 150 ml water added. Methylene chloride layer separated, dried over $MgSO_4$, filtered and solvent removed in vacuo leaving an amber foam. This foam was taken up in hot isopropanol. When cool, filtered 4.4 g of white crystals, mp 133°–136° C., plus small amount of higher melting material. Further recrystallization did not remove higher melting material. Solid was chromatographed through silica gel with chloroform as eluant. Fractions 10 and 11 held product. Evaporation of solvent gave 2.6 g of white crystals, mp 141°–143° C.

Anal. calc'd for $C_{18}H_{21}ClN_2O_2S$(%): Calc'd: C, 59.25; H, 5.80; N, 7.68; Found: C, 59.11; H, 5.82; N, 7.69.

The product was identified as N-(2,6-dimethyl-1-cyclohexen-1-yl)-N-[(2-oxo-3(2H)-benzothiazolyl)methyl]-2-chloroacetamide.

The starting materials used in the processes of this invention are well know. Thus, the sec-amide starting materials of the type used in Example 1 are disclosed in U.S. Pat. No. 3,574,746. The benzothiazolinone derivative is disclosed in U.S. Pat. No. 3,050,526.

EXAMPLE 2

This example illustrates an alternative and novel process for preparing compounds according to this invention.

N-(chloromethyl)-2'-methoxy-6'-methyl-2-chloroacetanilide, 3.6 g (0.0137 mol), in 100 ml of $CH_2Cl_2$ were mixed with benzothiazolin-2-one, 2.2 g (0.0145 mol) and 1.0 g benzyl triethyl ammonium bromide. To this mixture with stirring was added 30 ml of 50% caustic; the mixture was allowed to react for about three hours. On work up 5.8 g crude product was isolated, then recrystallized from isopropanol to a light buff-colored solid, m.p. 120°–121° C.

Anal. calc'd for $C_{18}H_{17}ClN_2O_3S$(%): Calc'd: C, 57.37; H, 4.55; N, 7.43; Found: C, 56.89; H, 4.51; N, 7.34.

The product was identified as N-(2'-methoxy-6'-methyl)-N-[(2-oxo-3(2H)-benzothiazolyl)methyl]-2-chloroacetanilide.

The benzothiazolin-2-one is a commercially-available product and the N-(chloromethyl)-2-chloroacetanilide derivative may be prepared by the conventional process of chloroacetylating the corresponding substituted phenylazomethine as described, e.g., in U.S. Pat. Nos. 3,637,847 and 3,547,620.

EXAMPLES 3–11

Following the same general procedures described in Examples 1 and 2, but subtituting the appropriate starting materials and reaction conditions, other 2-haloacetamides according to Formula I above are prepared. The same or equivalent solvents, bases and catalysts, together with appropriate temperatures and times are readily used in these process embodiments. Typical other compounds prepared in accordance with the above procedures are shown in Table I together with certain of their physical properties.

TABLE I

| Example No. | Compound | Empirical Formula | M.P. °C. | Analysis | | |
|---|---|---|---|---|---|---|
| | | | | Element | Calc'd. | Found |
| 3 | N—[(2-oxo-3(2H)—benzothiazolyl)methyl]-2'-6'-diethyl-2-chloroacetanilide | $C_{18}C_{17}ClN_2O_2S$ | 152–153 | C<br>H<br>N | 51.91<br>4.75<br>7.76 | 51.95<br>4.77<br>7.77 |
| 4 | N—[(2-oxo-3(2H)—benzothiazolyl)methyl]-N—(2-ethyl-6-methyl-1-cyclohexen-1-yl)-2-chloro-acetamide, mixed with its -N—[(2-oxo-3(2H)—benzothiazolyl)methyl]-N—(2-methyl-6-ethyl-1-cyclohexen-1-yl)-2-chloroacetamide | $C_{19}H_{23}ClN_2O_2S$ | 135–160 | C<br>H<br>N | 60.23<br>6.12<br>7.39 | 60.29<br>6.15<br>7.37 |
| 5 | N—[(2-oxo-3(2H)—benzothiazolyl)methyl]-N—(2,6-diethyl-1-cyclohexen-1-yl)-2-chloroacetamide | $C_{20}H_{25}ClN_2O_2S$ | 147–148 | C<br>H<br>N | 61.13<br>6.41<br>7.13 | 60.87<br>6.40<br>7.05 |
| 6 | N—[(5-chloro-2-oxo-3(2H)—benzothiazolyl)methyl]-N—(2,6-dimethyl-1-cyclohexen-1-yl)-2-chloroacetamide | $C_{18}H_{20}Cl_2N_2O_2S$ | 183–187 | C<br>H<br>N | 54.12<br>5.05<br>7.02 | 53.98<br>5.11<br>6.98 |
| 7 | N—[(6-bromo-2-oxo-3(2H)—benzothiazolyl)methyl]-N—(2,6-dimethyl-1-cyclohexen-1-yl)-2-chloroacetamide | $C_{18}H_{20}BrCN_2O_2S$ | 125–127 | C<br>H<br>N | 48.72<br>4.54<br>6.31 | 48.83<br>4.58<br>6.29 |
| 8 | N—[(6-ethoxy-2-oxo-3(2H)—benzothiazolyl)methyl]-N—(2,3-dimethyl-1-cyclohexen-1-yl)- | $C_{20}H_{25}ClN_2O_2S$ | 135–137 | C<br>H<br>N | 58.74<br>6.16<br>6.85 | 58.82<br>6.19<br>6.82 |

TABLE I-continued

| Example No. | Compound | Empirical Formula | M.P. °C. | Analysis Element | Calc'd | Found |
|---|---|---|---|---|---|---|
| 9 | 2-chloroacetamide N—[(2-oxo-3(2H)—benzothiazolyl)methyl]-N—(2,6-dimethyl-1-cyclohexen-1-yl)-2-chloroamide | $C_{18}H_{25}ClN_2O_2S$ | 95–99 | C H N | 58.60 6.83 7.59 | 58.65 6.83 7.58 |
| 10 | N—[(2-oxo-3(2H)—benzothiazolyl)methyl]-N—(2-methyl-1-cyclohexen-1-yl)-2-chloroamide | $C_{17}H_{19}ClN_2O_2S$ | 134–139 | C H N | 58.19 5.46 7.98 | 58.15 5.50 7.96 |
| 11 | N—[(2-oxo-3(2H)—benzoxazolyl)methyl]-N—(2,6-dimethyl-1-cyclohexen-1-yl)-2-chloroamide | $C_{18}H_{21}ClN_2O_3$ | 140–142 | C H N | 61.98 6.07 8.03 | 61.99 6.10 8.03 |

As noted above, the compounds of this invention have been found to be effective as herbicides, particularly as preemergence herbicides, although post-emergence activity has also been shown. Tables II and III summarize results of tests conducted to determine the pre-emergent herbicidal activity of the compounds of this invention.

The pre-emergence tests are conducted as follows:

A good grade of top soil is placed in aluminum pans and compacted to a depth of three-eighths to one-half inch from the top of the pan. On the top of the soil is placed a predetermined number of seeds or vegetative propagules of various plant species. The soil required to level fill the pans after seeding or adding vegetative propagules is weighed into a pan. A known amount of the active ingredient applied in a solvent or as a wettable powder suspension and the soil are thoroughly mixed, and used as a cover layer for prepared pans. After treatment, the pans are moved into a greenhouse bench where they are watered from below as needed to give adequate moisture for germination and growth.

Approximately 2–3 weeks after seeding and treating, the plants are observed and the results recorded. Table II below summarizes such results. The herbicidal rating is obtained by means of fixed scale based on the percent injury of each plant species. The ratings are defined as follows:

| % Control | Rating |
|---|---|
| 0–24 | 0 |
| 25–49 | 1 |
| 50–74 | 2 |
| 75–100 | 3 |

The plant species utilized in one set of tests, the data for which are shown in Table II, are identified by letter in accordance with the following legend:

| | | |
|---|---|---|
| A Canada Thistle | E Lambsquarters | I Johnsongrass |
| B Cocklebur | F Smartweed | J Downy Brome |
| C Velvetleaf | G Yellow Nutsedge | K Barnyardgrass |
| D Morningglory | H Quackgrass | |

TABLE II

| Compound of Example No. | Kg/ha | Pre-Emergent Plant Species | | | | | | | | | | |
|---|---|---|---|---|---|---|---|---|---|---|---|---|
| | | A | B | C | D | E | F | G | H | I | J | K |
| 1 | 11.0 | 0 | 0 | 0 | 2 | 0 | 3 | 2 | 2 | 3 | 2 | 3 |
| | 5.6 | 0 | 1 | 0 | 2 | 1 | 1 | 0 | 2 | 0 | 2 | 3 |
| 2 | 11.2 | 0 | 0 | 0 | 0 | 1 | 0 | 3 | 1 | 0 | 2 | 3 |
| | 5.6 | 0 | 0 | 0 | 0 | 1 | 0 | 3 | 2 | 0 | 1 | 3 |
| 3 | 11.2 | 0 | 0 | 0 | 0 | 0 | 0 | 1 | 1 | 0 | 1 | 3 |
| | 5.6 | 0 | 0 | 0 | 0 | 0 | 0 | 1 | 0 | 0 | 1 | 3 |
| 4 | 11.2 | 2 | 0 | 0 | 0 | 3 | 0 | 0 | 0 | 3 | 1 | 3 |
| | 5.6 | 1 | 0 | 0 | 0 | 1 | 0 | 0 | 0 | 0 | 1 | 3 |
| 5 | 11.2 | 0 | 0 | 0 | 0 | 1 | 0 | 0 | 0 | 0 | 0 | 1 |
| | 5.6 | 0 | 0 | 0 | 0 | 1 | 0 | 0 | 0 | 0 | 0 | 1 |
| 6 | 11.2 | 1 | 0 | 0 | 0 | 3 | 0 | 0 | 1 | 0 | 0 | 3 |
| | 5.6 | 0 | 0 | 0 | 0 | 0 | 0 | 0 | 0 | 0 | 0 | 1 |
| 7 | 11.2 | 0 | 0 | 0 | 0 | 1 | 0 | 0 | 0 | 0 | 0 | 1 |
| | 5.6 | 0 | 0 | 0 | 0 | 0 | 0 | 0 | 0 | 0 | 0 | 1 |
| 8 | 11.2 | 0 | — | 0 | 0 | 0 | 0 | 0 | 0 | 0 | 0 | 0 |
| | 5.6 | 0 | 0 | 0 | 0 | 0 | 0 | 0 | 0 | 0 | 0 | 1 |
| 9 | 11.2 | 0 | 0 | 0 | 0 | 1 | 3 | 0 | 1 | 0 | 2 | 3 |
| | 5.6 | 0 | 0 | 0 | 0 | 1 | 0 | 0 | 0 | 0 | 0 | 3 |
| 10 | 11.2 | 0 | 0 | 0 | 1 | 0 | 0 | 1 | 0 | 0 | 3 | 3 |
| | 5.6 | 0 | 0 | 0 | 3 | 0 | 0 | 1 | 3 | 0 | 3 | 3 |
| 11 | 11.2 | 0 | 0 | 0 | 0 | 1 | 0 | 1 | 3 | 0 | 3 | 3 |
| | 5.6 | 0 | 0 | 0 | 0 | 2 | 0 | 3 | 1 | 0 | 3 | 3 |

The compounds were further tested by utilizing the above procedure on the following plant species:

| | |
|---|---|
| L Soybean | R Hemp Sesbania |
| M Sugarbeet | E Lambsquarters |
| N Wheat | F Smartweed |
| O Rice | C Velvetleaf |
| P Sorghum | J Downy Brome |
| B Cocklebur | S Panicum |
| Q Wild Buckwheat | K Barnyardgrass |
| D Morningglory | T Crabgrass |

The results are summarized in Table III.

TABLE III

| Compound of Example No. | kg/ha | Pre-Emergent Plant Species | | | | | | | | | | | | | |
|---|---|---|---|---|---|---|---|---|---|---|---|---|---|---|---|
| | | L | M | N | O | P | B | Q | D | R | E | F | C | J | S | K | T |
| 1 | 5.6 | 1 | 1 | 0 | 2 | 1 | — | 0 | 0 | — | 1 | 0 | 0 | 2 | 3 | 3 |
| | 1.12 | 0 | 1 | 1 | 2 | 3 | — | 0 | 0 | — | 2 | 0 | 0 | 3 | 3 | 3 |
| | 0.28 | 0 | 1 | 0 | 2 | 0 | — | 0 | 0 | — | 2 | 1 | 0 | 3 | 3 | 3 |
| | 0.056 | 1 | 1 | 0 | 0 | 0 | 0 | 0 | 1 | 0 | 1 | 1 | 0 | 3 | 3 | 3 |
| | 0.0112 | 0 | 0 | 0 | 1 | 0 | 0 | 0 | 3 | 1 | 1 | 0 | 1 | 3 | 3 | 2 |
| | 0.0056 | 0 | 0 | 0 | 1 | 0 | — | 0 | 3 | — | 1 | 1 | 0 | 3 | 3 | 3 |

TABLE III-continued

| Compound of Example No. | kg/ha | \multicolumn{16}{c}{Pre-Emergent Plant Species} |
|---|---|---|---|---|---|---|---|---|---|---|---|---|---|---|---|---|---|
| | | L | M | N | O | P | B | Q | D | R | E | F | C | J | S | K | T |
| 2 | 5.6 | 0 | 0 | 2 | 3 | 1 | 0 | 0 | 0 | 2 | 1 | 2 | 0 | 3 | 3 | 3 | 3 |
|  | 1.12 | 0 | 0 | 0 | 3 | 1 | 0 | 0 | 0 | 0 | 3 | 2 | 0 | 3 | 3 | 3 | 3 |
|  | 0.28 | 0 | 0 | 0 | 1 | 0 | 0 | 0 | 0 | 0 | 2 | 1 | 0 | 1 | 1 | 3 | 1 |
|  | 0.056 | 0 | 0 | 0 | 0 | 0 | 0 | 0 | 0 | 0 | 0 | 0 | 0 | 0 | 2 | 2 | 0 |
|  | 0.0112 | 0 | 0 | 0 | 0 | 0 | 0 | 0 | 0 | 0 | 0 | 0 | 0 | 0 | 0 | 0 | 0 |
| 3 | 5.6 | 0 | 0 | 0 | 0 | 0 | 0 | 0 | 0 | 0 | 0 | 0 | 0 | 2 | 3 | 3 | 3 |
|  | 1.12 | 0 | 0 | 0 | 0 | 0 | 0 | 0 | 0 | 0 | 0 | 1 | 0 | 1 | 1 | 3 | 2 |
|  | 0.28 | 0 | 0 | 0 | 1 | 0 | 0 | 0 | 0 | 0 | 0 | 0 | 0 | 0 | 0 | 3 | 1 |
| 4 | 5.6 | 0 | 1 | 0 | 1 | 0 | 3 | 0 | 1 | 3 | 3 | 3 | 0 | 0 | 2 | 3 | 3 |
|  | 1.12 | 0 | 0 | 0 | 0 | 0 | 0 | 0 | 0 | 0 | 2 | 3 | 0 | 0 | 0 | 3 | 3 |
|  | 0.28 | 0 | 1 | 0 | 0 | 0 | — | 0 | 1 | 0 | 0 | 0 | 0 | 0 | 0 | 0 | 2 |
| 6 | 5.6 | 0 | 1 | 0 | 0 | 0 | 0 | 0 | 0 | 3 | 1 | 1 | 0 | 0 | 0 | 1 | 3 |
|  | 1.12 | 0 | 1 | 0 | 1 | 0 | 0 | 0 | 0 | 3 | 3 | 2 | 0 | 0 | 0 | 0 | 2 |
| 9 | 5.6 | 0 | 1 | 2 | 2 | 2 | — | 0 | 0 | 0 | 1 | 1 | 0 | 2 | 3 | 3 | 3 |
|  | 1.12 | 0 | 0 | 0 | 2 | 0 | 0 | 0 | 0 | 0 | 0 | 0 | 0 | 0 | 0 | 3 | 2 |
|  | 0.26 | 0 | 0 | 0 | 0 | 0 | 0 | 0 | — | — | 0 | 0 | 0 | 0 | 0 | 2 | 1 |
| 10 | 5.6 | 0 | 0 | 1 | 3 | 0 | 0 | 0 | 0 | 0 | 3 | 2 | 0 | 2 | 2 | 3 | 3 |
|  | 1.12 | 0 | 0 | 0 | 0 | 0 | 0 | 0 | 0 | 0 | 1 | 1 | 0 | 0 | 0 | 2 | 3 |
|  | 0.28 | 0 | 0 | 0 | 0 | 0 | 0 | 0 | 0 | 0 | 0 | 0 | 0 | 0 | 0 | 3 | 3 |
|  | 0.056 | 0 | 0 | 0 | 0 | 0 | 0 | 0 | 0 | 0 | 1 | 0 | 0 | 0 | 0 | 3 | 3 |

EXAMPLES 12-45

The compounds in the following examples may also be prepared by substantial repetition of the general procedures described in Examples 1 and 2, modified as to starting materials, reaction temperatures, times, solvents, catalysts, bases, etc., to account for the nature of the particular reactants, as will be apparent to those skilled in the art. In Tables IV and V, the individual compounds are those whose members are identified by the generic formulae. In Table IV, Formula IA relates to compounds wherein R is characterized by substituted or unsubstituted 1-cycloalken-1-yl radicals; in Table V, Formula IB relates to compounds wherein R is characterized by substituted or unsubstituted phenyl radicals.

TABLE IV

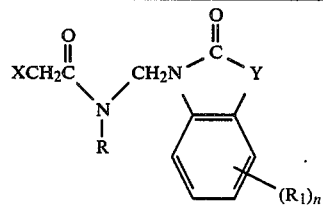

IA

| Cpd. of Ex. No. | X | Y | n | R₁ | R |
|---|---|---|---|---|---|
| 12 | Cl | O | 0 | — | 2-methyl-6-methoxy-1-cyclopenten-1-yl |
| 13 | Br | S | 1 | 4-CH₃ | 2-ethyl-1-cyclohexen-1-yl |
| 14 | Cl | N—CH₃ | 0 | — | 2-methoxymethyl-6-methyl-1-cyclohexen-1-yl |
| 15 | Cl | N—H | 1 | 5-OCH₃ | 1-cyclohepten-1-yl |
| 16 | Br | S | 3 | 4,5,6-trimethyl | 2,6-dimethyl-1-cyclohexen-1-yl |
| 17 | Cl | S | 1 | 4-SCH₃ | 2,6-diethyl-1-cyclopenten-1-yl |
| 18 | Cl | S | 0 | — | 2-allyl-1-cyclohepten-1-yl |
| 19 | Br | S | 0 | — | 2-propargyl-6-methyl-1-cyclohexen-1-yl |
| 20 | Cl | O | 0 | — | 2-CF₃—6-methyl-1-cyclohexen-1-yl |
| 21 | Br | S | 3 | 4,5,6-trimethyl | 2-chloro-6-methyl-1-cyclopenten-1-yl |

TABLE IV-continued

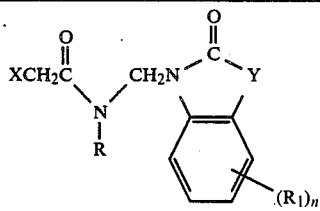

IA

| Cpd. of Ex. No. | X | Y | n | R₁ | R |
|---|---|---|---|---|---|
| 22 | Cl | N—C₃H₇ | 0 | — | 2-NO₂—6-methyl-1-cyclohepten-1-yl |
| 23 | Cl | S | 1 | 4-furfuryl | 2,6-dimethyl-1-cyclohexen-1-yl |
| 24 | Cl | S | 0 | — | 2-furfuryl-6-ethyl-1-cyclohexen-1-yl |
| 25 | Cl | S | 1 | 5-allyl | 3-tetrahydrofurfuryl-6-n-propyl-1-cyclohexen-1-yl |
| 26 | Cl | S | 0 | — | 2,5-dimethyl-1-cyclopenten-1-yl |
| 27 | Cl | S | 0 | — | 2-methyl-1-cyclopenten-1-yl |

TABLE V

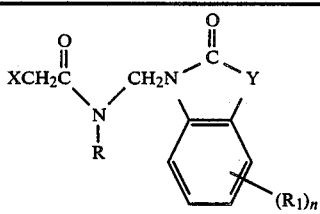

IB

| Cpd. of Ex. No. | X | Y | n | R₁ | R |
|---|---|---|---|---|---|
| 28 | Cl | S | 0 | — | 2,6-dimethylphenyl |
| 29 | Br | S | 1 | 6-Cl | 2-methyl-6-ethylphenyl |
| 30 | Br | S | 2 | 5,6-diCl | 2-t-butyl-6-chlorophenyl |
| 31 | Cl | O | 0 | — | 2-methylthio-6- |

TABLE V-continued

IB $$XCH_2\overset{O}{\underset{\|}{C}}-\underset{\underset{R}{|}}{N}-CH_2N\overset{\overset{O}{\|}}{\underset{}{C}}-Y$$

(R₁)ₙ on phenyl ring

| Cpd. of Ex. No. | X | Y | n | R₁ | R |
|---|---|---|---|---|---|
| 32 | Cl | O | 1 | 4-phenyl | 2-nitrophenyl methylphenyl |
| 33 | Br | NH | 0 | — | 2-benzyl-6-methylphenyl |
| 34 | Cl | NCH₃ | 1 | 5-furfuryl | phenyl |
| 35 | Cl | N—n-C₄H₉ | 0 | — | 2-CF₃—6-ethyl-phenyl |
| 36 | Cl | S | 3 | 4,5,6-trimethyl | 2,3-dimethyl-phenyl |
| 37 | Cl | S | 0 | — | 2-propargyl-6-ethylphenyl |
| 38 | Cl | O | 1 | 4-NO₂ | 2-methoxy-methyl-6-methylphenyl |
| 39 | Cl | S | 0 | — | 2-(2-methoxy-ethoxy)-6-methylphenyl |
| 40 | Cl | S | 1 | 4-Br | 2-allyl-6-methoxyphenyl |
| 41 | Cl | S | 0 | — | 2-t-butyl-6-chlorophenyl |
| 42 | Cl | S | 1 | 4-ethoxy | 2-tetrahydro-furfuryl-6-ethylphenyl |
| 43 | Cl | S | 0 | — | 2-furfuryl-6-n-propylphenyl |
| 44 | Cl | S | 0 | — | 2-methyl-6-isobutoxyphenyl |
| 45 | Cl | S | 0 | — | 2-(trifluoro-methyl)-6-methylphenyl |

The compound of Example 1 has been found to be particularly efficacious as a rice herbicide. In Table VI, data is presented showing the effect of said compound on the major Asian rice weeds *Echinochloa crusgalli* (EC), *Monochoria vaginalis* (MV), *Cyperus serotinus* (CS), *Eleocharis kuroguwai* (EK) and *Sagittaria trifolia* (ST) in transplanted rice at rates within the range of 0.25–2.0 lb/A (0.28–2.24 kg/ha); observations were made 18 days after treatment.

TABLE VI

| Compound of Example No. | Rate (Kg/Ha) | Percent Inhibition | | | | | |
|---|---|---|---|---|---|---|---|
| | | Rice | EC | MV | CS | EK | ST |
| 1 | 2.24 | 10 | 100 | 100 | 100 | 100 | 5 |
| | 1.12 | 0 | 100 | 100 | 100 | 100 | 5 |
| | 0.56 | 0 | 100 | 100 | 90 | 100 | 5 |
| | 0.28 | 0 | 100 | 100 | 80 | 100 | 0 |

It is thus seen that the compound of Example 1 selectively controlled all weeds in the test, except *Sagittaria trifolia* at rates as low as 0.28 kg/ha, the minimum test rate, while maintaining rice safety (i.e., 15% or less injury) at 2.24 kg/ha or more.

The herbicidal compositions of this invention including concentrates which require dilution prior to application contain at least one active ingredient and an adjuvant in liquid or solid form. The compositions are prepared by admixing the active ingredient with an adjuvant including diluents, extenders, carriers and conditioning agents to provide compositions in the form of finely-divided particulate solids, granules, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these.

The compositions of this invention, particularly liquids and wettable powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and non-ionic agents can be used with equal facility.

Preferred wetting agents are alkyl benzene and alkyl napthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene deriviatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl, napthalene sulfonates, sodium naphthalene sulfonate, and the polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from about 0.5 to 60 parts (preferably from 5–20 parts) of active ingredient, from about 0.25 to 25 parts (preferably 1–15 parts) of wetting agent, from about 0.25 to 25 parts (preferably 1.0–15 parts) of dispersant and from 5 to about 95 parts (preferably 5–50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1–10% by weight.

Aqueous suspensions or emulsions may be prepared by stirring an aqueous mixture of a water-insoluble active ingredient and an emulsification agent until uniform and then homogenized to give stable emulsion of very finely-divided particles. The resulting concentrated aqueous suspension is characterized by its extremely small particle size, so that when diluted and sprayed, coverage is very uniform. Suitable concentrations of the formulations contain from about 0.1–60% preferably 5–50% by weight of active ingredient, the upper limit being determined by the solubility limit of active ingredient in the solvent.

In another form of aqueous suspensions, a water-immiscible herbicide is encapsulated to form microencapsulated phase dispersed in an aqueous phase. In one embodiment, minute capsules are formed by bringing together an aqueous phase containing a lignin sulfonate emulsifier and a water-immiscible chemical and polymethylene polyphenylisocyanate, dispersing the water-immiscible phase in the aqueous phase followed by addition of a polyfunctional amine. The isocyanate and amine compounds react to form a solid urea shell wall around particles of the water-immiscible chemical, thus forming microcapsules thereof. Generally, the concentration of the microencapsulated material will range from about 480 to 700 g/l of total composition, preferably 480 to 600 g/l. The microencapsulation process referred to here is described in more detail in the assignee's copending U.S. Ser. No. 23,566 filed Mar. 26, 1979.

Concentrates are usually solutions of active ingredient in water-immiscible or partially water-immiscible solvents together with a surface active agent. Suitable solvents for the active ingredient of this invention include dimethylformide, dimethylsulfoxide, N-methylpyrrolidone, hydrocarbons amd water-immiscible ethers, esters or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention include, for example, triazines, ureas, carbamates, acetamides, acetanilides, uracils, acetic acid or phenol derivatives, thiolcarbamates, triazoles, benzoic acids, nitriles, biphenyl ethers and the like such as:

Heterocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-isopropyl-1H-2,1,3-benzothiadiazin-4-(3H)-one 2,2-dioxide
3-Amino-1,2,4-triazole
6,7-Dihydrodipyrido(1,2-a:2',1'-c)-pyrazidiinium salt
5-Bromo-3-isopropyl-6-methyluracil
1,1'-Dimethyl-4,4'-bipyridinium Ureas N'-(4-chlorophenoxy)phenyl-N,N-dimethylurea
N,N-dimethyl-N'-(3-chloro-4-methylphenyl)urea
3-(3,4-dichlorophenyl)-1,1-dimethylurea
1,3-Dimethyl-3-(2-benzothiazolyl)urea
3-(p-Chlorophenyl)-1,1-dimethylurea
1-Butyl-3-(3,4-dichlorophenyl)-1-methylurea Carbamates/Thiolcarbamates 2-Chloroallyl diethyldithiocarbamate
S-(4-chlorobenzyl)N,N-diethylthiolcarbamate
Isopropyl N-(3-chlorophenyl)carbamate
S-2,3-dichloroallyl N,N-diisopropylthiolcarbamate
Ethyl N,N-dipropylthiolcarbamate
S-propyl dipropylthiolcarbamate Acetamides/Acetanilides/Anilines/Amides 2-Chloro-N,N-diallylacetamide
N,N-dimethyl-2,2-diphenylacetamide
N-(2,4-dimethyl-5-[[(trifluoromethyl)sulfonyl]amino]-phenyl)acetamide
N-isopropyl-2-chloroacetanilide
2',6'-Diethyl-N-methoxymethyl-2-chloroacetanilide
2'-Methyl-6'-ethyl-N-(2-methoxyprop-2-yl)-2-chloroacetanilide
$\alpha,\alpha,\alpha$-Trifluoro-2,6-dinitro-N,N-dipropyl-p-toluidine
N-(1,1-dimethylpropynyl)-3,5-dichlorobenzamide Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol
N-(phosphonomethyl)glycine and its $C_{1-6}$ monoalkyl amine and alkaline metal salts and combinations thereof Ethers 2,4-Dichlorophenyl-4-nitrophenyl ether
2-Chloro-$\alpha,\alpha,\alpha$-trifluoro-p-tolyl-3-ethoxy-4-nitrodiphenyl ether Miscellaneous 2,6-Dichlorobenzonitrile
Monosodium acid methanearsonate
Disodium methanearsonate Fertilizers useful in combination with the active ingredients include, for example, ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

|  | Weight Percent |
|---|---|
| I. Emulsifiable Concentrates | |
| A. Compound of Example No. 1 | 1.0 |
| Free acid of complex organic phosphate of aromatic or aliphatic hydrophobe base (e.g., GAFAC RE-610, registered trademark of GAF Corp) | 5.59 |
| Polyoxyethylene/polyoxypropylene block copolymer with butanol (e.g., Tergitol XH, registered trademark of Union Carbide Corp.) | 1.11 |
| Phenol | 5.34 |
| Monochlorobenzene | 77.16 |
|  | 100.00 |
| B. Compound of Example No. 4 | 25.00 |
| Free acid of complex organic phosphate of aromatic or aliphatic hydrophobe base (e.g., GAFAC RE-610) | 5.00 |
| Polyoxyethylene/polyoxypropylene block copolymer with butanol (e.g., Tergitol XH) | 1.60 |
| Phenol | 4.75 |
| Monochlorobenzene | 63.65 |
|  | 100.00 |
| II Flowables | |
| A. Compound of Example No. 1 | 25.00 |
| Methyl cellulose | 0.3 |
| Silica aerogel | 1.5 |
| Sodium lignosulfonate | 3.5 |
| Sodium N—methyl-N—oleyl-taurate | 2.0 |
| Water | 66.7 |
|  | 100.00 |
| B. Compound of Example 4 | 45.0 |
| Methyl cellulose | .3 |
| Silica aerogel | 1.5 |
| Sodium lignosulfonate | 3.5 |
| Sodium N—methyl-N—oleyl taurate | 2.0 |
| Water | 47.3 |
|  | 100.00 |
| III. Wettable Powders | |
| A. Compound of Example No. 2 | 25.0 |
| Sodium lignosulfonate | 3.0 |
| Sodium N—methyl-N—oleyl-taurate | 1.0 |
| Amorphous silica (synthetic) | 71.0 |
|  | 100.00 |
| B. Compound of Example No. 3 | 80.0 |
| Sodium dioctyl sulfosuccinate | 1.25 |
| Calcium lignosulfonate | 2.75 |
| Amorphous silica (synthetic) | 16.00 |
|  | 100.00 |
| C. Compound of Example No. 6 | 10.0 |
| Sodium lignosulfonate | 3.0 |
| Sodium N—methyl-N—oleyl-taurate | 1.0 |
| Kaolinite clay | 86.0 |
|  | 100.00 |
| IV. Water-Soluble Powders | |
| A. Compound of Example 1 | 10.0 |
| Sodium dioctyl sulfosuccinate | 2.0 |
| Silica aerogel | 5.0 |
| Methyl violet | 0.1 |
| Sodium bicarbonate | 82.9 |
|  | 100.00 |
| B. Compound of Example 4 | 90.0 |
| Ammonium phosphate | 10.0 |
|  | 100.00 |
| V. Dusts | |
| A. Compound of Example No. 2 | 2.0 |
| Attapulgite | 98.0 |
|  | 100.00 |
| B. Compound of Example No. 3 | 60.0 |
| Montmorillonite | 40.0 |
|  | 100.0 |
| C. Compound of Example No. 6 | 30.0 |
| Ethylene glycol | 1.0 |
| Bentonite | 69.0 |
|  | 100.00 |
| D. Compound of Example No. 10 | 1.0 |
| Diatomaceous earth | 99.0 |
|  | 100.00 |
| VI. Granules | |
| A. Compound of Example No. 1 | 15.0 |
| Granular attapulgite (20/40 mesh) | 85.0 |
|  | 100.00 |
| B. Compound of Example No. 4 | 30.0 |
| Diatomaceous earth (20/40) | 70.0 |
|  | 100.00 |
| C. Compound of Example No. 6 | 1.0 |
| Ethylene glycol | 5.0 |
| Methylene blue | 0.1 |
| Pyrophyllite | 93.9 |
|  | 100.00 |
| D. Compound of Example No. 10 | 5.0 |
| Pyrophyllite (20/40) | 95.0 |
|  | 100.00 |

When operating in accordance with the present invention, effective amounts of the acetanilides of this invention are applied to the soil containing the plants, or are incorporated into aquatic media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds of this invention to the locus of undesired weeds is essential and critical for the practice of the present invention. The exact amount of active ingredient to be employed is dependent upon various factors, including the plant species and stage of development thereof, the type and condition of soil, the amount of rainfall and the specific acetanilide employed. In selective preemergence application to the plants or to the soil a dosage of from 0.02 to about 11.2 kg/ha, preferably from about 0.04 to about 5.60 kg/ha, or suitably from 1.12 to 5.6 kg/ha of acetanilide is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in Webster's New International Dictionary, Second Edition, Unabridged (1961). Thus the term refers to any substance or media in which vegetation may take root and grow, and includes not only earth but also compost, manure, muck, humus, sand and the like, adapted to support plant growth.

Although the invention is described with respect to specific modifications, the details thereof are not to be construed as limitations except to the extent indicated in the following claims.

What is claimed is:

1. Compounds having the formula

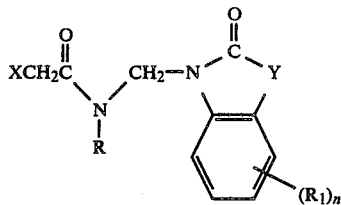

wherein

X is chlorine, bromine or iodine;

R is a $C_{5-7}$ cycloalkenyl or phenyl radical or such R radical independently substituted with $C_{1-6}$ alkyl, thioalkyl or, alkoxy $C_2$-$C_6$, alkoxyalkyl, or polyalkoxy, $C_{2-6}$ alkenyl or alkynyl, $C_{6-10}$ aryl, halogen, $NO_2$, $CF_3$ or a $C_{5-6}$ heterocyclic ring having only one O or S hetero atom;

Y is O or S;

$R_1$ is hydrogen, halogen, $C_{1-6}$ alkyl, thioalkyl, alkoxy, allyl, or furfuryl; and n is an integer from 0-4 inclusive.

2. Compounds according to claim 1 wherein R is a $C_{1-6}$ alkyl-substituted 1-cycloalken-1-yl radical, n is zero, X is chlorine and Y is sulfur.

3. Compound having the formula N-(2,6-dimethyl-1-cyclohexen-1-yl)-N-[(2-oxo-3(2H)-benzothiazolyl)methyl]-2-chloroacetamide.

4. Compounds according to claim 1 wherein R is phenyl substituted with $C_{1-6}$ alkyl or alkoxy, n is zero, X is chlorine and Y is sulfur.

5. Compound according to claim 4 which is N-[2-oxo-3(2H)-benzothiazolyl)methyl]-2'-methoxy-6'-methyl-2-chloroacetanilide.

6. Compound according to claim 4 which is N-[(2-oxo-3(2H)-benzothiazolyl)methyl]-2',6'-diethyl-2-chloroacetanilide.

* * * * *